US008795173B2

(12) United States Patent
Poh et al.

(10) Patent No.: US 8,795,173 B2
(45) Date of Patent: Aug. 5, 2014

(54) METHODS AND APPARATUS FOR ASSESSMENT OF ATYPICAL BRAIN ACTIVITY

(75) Inventors: Ming-Zher Poh, Cambridge, MA (US); Rosalind Picard, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/474,704

(22) Filed: May 17, 2012

(65) Prior Publication Data

US 2012/0296175 A1  Nov. 22, 2012

Related U.S. Application Data

(60) Provisional application No. 61/486,896, filed on May 17, 2011.

(51) Int. Cl.
| | |
|---|---|
| A61B 5/00 | (2006.01) |
| A61B 5/024 | (2006.01) |
| A61B 5/11 | (2006.01) |
| A61B 5/053 | (2006.01) |

(52) U.S. Cl.
CPC ........... *A61B 5/4094* (2013.01); *A61B 5/02405* (2013.01); *A61B 5/1118* (2013.01); *A61B 5/7275* (2013.01); *A61B 5/0533* (2013.01)
USPC ....................................................... 600/301

(58) Field of Classification Search
USPC ....................................................... 600/301
See application file for complete search history.

(56) References Cited

U.S. PATENT DOCUMENTS

| | | | |
|---|---|---|---|
| 7,269,455 | B2 | 9/2007 | Pineda |
| 7,282,028 | B2 * | 10/2007 | Kim et al. ..................... 600/300 |
| 7,324,851 | B1 | 1/2008 | DiLorenzo |
| 2005/0107655 | A1 | 5/2005 | Holzner |
| 2006/0265022 | A1 | 11/2006 | John et al. |
| 2008/0146958 | A1 * | 6/2008 | Guillory et al. ............... 600/544 |
| 2008/0214903 | A1 * | 9/2008 | Orbach ......................... 600/301 |
| 2008/0319505 | A1 | 12/2008 | Boyden et al. |

(Continued)

OTHER PUBLICATIONS

International Search Report and Written Opinion, Aug. 31, 2012, PCT application # PCT/US12/38463, international filing date May 17, 2012.

J. Van Buren, Some Autonomic Concomitants of Ictal Automatism; A Study of Temporal Lobe Attacks, Brain 81(4), pp. 505-528 (Dec. 1958).

J. Frost, R. Hrachovy, P. Kellaway, T. Zion, Quantitative Analysis and Characterization of Infantile Spasms, Epilepsia, Jun. 1978, 19(3), pp. 273-282.

(Continued)

*Primary Examiner* — Bill Thomson
*Assistant Examiner* — Sebastian X Lukjan
(74) *Attorney, Agent, or Firm* — Stephen R. Otis

(57) ABSTRACT

In exemplary implementations of this invention, sensor measurements are taken before, during and after an epileptiform seizure of a human. The sensors measure electrodermal activity (EDA) and heart rate variability (HRV) of the human. The EDA and HRV measurements are used to assess sympathetic activity and parasympathetic activity, respectively. More particularly, in the case of HRV measurements, HF power is used to assess parasympathetic innervation of the heart. HF power is the power of the high frequency (e.g. 0.15 to 0.4 Hz) spectral component of the RRI signal.

One or more processors analyze the sensor data to calculate the magnitude of a post-ictal autonomic disturbance. Based on that calculated magnitude, the processors assess the severity of the seizure.

A wrist-worn sensor may take long-term, continuous EDA and motion measurements. The processors may analyze these measurements to detect the onset of a tonic-clonic seizure.

22 Claims, 11 Drawing Sheets

(56) References Cited

U.S. PATENT DOCUMENTS

| | | | |
|---|---|---|---|
| 2009/0058660 A1 | 3/2009 | Torch | |
| 2010/0198289 A1* | 8/2010 | Kameli et al. | 607/14 |
| 2010/0268056 A1 | 10/2010 | Picard et al. | |
| 2010/0280335 A1 | 11/2010 | Carlson et al. | |
| 2010/0280574 A1 | 11/2010 | Carlson et al. | |
| 2010/0280579 A1* | 11/2010 | Denison et al. | 607/62 |
| 2011/0004072 A1 | 1/2011 | Fletcher et al. | |
| 2011/0306846 A1* | 12/2011 | Osorio | 600/301 |

OTHER PUBLICATIONS

Y. Nagai, L. Goldstein, P. Fenwick, M. Trimble, Clinical efficacy of galvanic skin response biofeedback training in reducing seizures in adult epilepsy: a preliminary randomized controlled study, Epilepsy & Behavior, Apr. 2004, 5(2), pp. 216-223.

Lhatoo, S., Faulkner, H., Dembny, K., Trippick, K., Johnson, C., and Bird, J. An electroclinical case-control study of sudden unexpected death in epilepsy. Annals of neurology, Dec. 2010, vol. 68, Issue 6, pp. 787-796.

* cited by examiner

METHODS AND APPARATUS FOR ASSESSMENT OF ATYPICAL BRAIN ACTIVITY

RELATED APPLICATIONS

This application claims the benefit of U.S. Provisional Application Ser. No. 61/486,896, filed May 17, 2011, the entire disclosure of which is herein incorporated by reference.

FIELD OF THE TECHNOLOGY

The present invention relates generally to the assessment of atypical brain activity.

BACKGROUND

Approximately 50 million people worldwide are affected by epilepsy, one of the most common serious neurological disorders that has potentially deadly consequences. Epilepsy is a disorder of the brain characterized predominantly by an enduring predisposition to generate epileptic seizures—transient manifestations of abnormal, excessive or synchronous neuronal activity in the brain. In America, the prevalence of epilepsy is estimated as 3 million with around 200,000 new cases diagnosed each year. Among all medical conditions, it is as common as lung or breast cancer. Moreover, death from seizure-related causes is comparable with breast cancer; up to 50,000 deaths occur every year in America

SUMMARY

In exemplary implementations of this invention, sensor measurements are taken before, during and after an epileptiform seizure of a human. The sensors measure electrodermal activity (EDA) and heart rate variability (HRV) of the human.

The EDA measurements are used to assess sympathetic activity; and HRV measurements are used to measure parasympathetic activity. More particularly, in the case of HRV measurements, HF (high frequency) power is used to assess parasympathetic innervation of the heart. HF power is the power of the high frequency (e.g. 0.15 to 0.4 Hz) spectral component of the RRI (R-R interval) signal. RRI is a measure of the inter-beat interval between two successive heat beats. More particularly, RRI measures the interval between two successive R spikes in a sequence of heart beats.

In exemplary implementations of this invention, one or more processors analyze the sensor data in order to calculate the magnitude of a post-ictal autonomic disturbance. Based on that calculated magnitude, the processors assess the severity of the seizure.

For example, the post-ictal autonomic disturbance may comprise a prolonged (e.g., at least 30 minutes) post-ictal surge in EDA and a prolonged, post-ictal decline in HF power. The processors may recognize the EDA surge/HF power decline, and, based on that surge/decline, determine that: (a) the seizure is severe (e.g., has a higher rating on a severity scale than it would have been in the absence of such surge/decline); (b) the seizure is more likely to be a tonic-clonic seizure, and less likely to be a complex partial seizure; than it would have been in the absence of the surge/decline, or (c) the seizure has a higher risk of SUDEP (sudden unexpected death in epilepsy) than it would have in the absence of such a surge/decline.

In some implementations of this invention, a wearable sensor takes continuous EDA and motion measurements over extensive periods of time. This device offers the ability to perform comfortable, long-term, and in situ assessment of EDA and motion. For example, the sensor may be wrist-worn, and the motion measurements may be taken by a tri-axis accelerometer (ACM). The processors may analyze the EDA and ACM data to detect the onset of a tonic-clonic seizure.

In some implementations, this invention not only detects the onset of a tonic-clonic seizure, but also evaluates the severity of the seizure.

The above description of the present invention is just a summary. It is intended only to give a general introduction to some illustrative implementations of this invention. It does not describe all of the details of this invention. This invention may be implemented in many other ways.

BRIEF DESCRIPTION OF THE DRAWINGS

FIG. 5A shows an example of a small increase of EDA that can occur during a complex partial seizure (CPS).

FIG. 5B shows an example of a large surge in EDA that can occur after a generalized tonic-clonic seizure (GTCS)

In FIG. 7A, a scatter plot shows an example of PGES duration versus EDA response amplitude.

In FIG. 7B, a scatter plot shows an example of log-transformed area under rising portion of EDA curve.

In FIG. 7C, a scatter plot shows an example of maximum percentage HF power change.

FIG. 7D shows an example in which EDA response amplitude is greater for GTCS with higher SUDEP risk than for GTCS with lower SUDEP risk.

FIG. 7E shows an example in which the maximum percentage decrease in HF power is greater in GTCS with higher SUDEP risk than in GTCS with lower SUDEP risk.

The above Figures illustrate some illustrative implementations of this invention, or provide information that relates to those implementations. However, this invention may be implemented in many other ways. The above Figures do not show all of the details of this invention.

DETAILED DESCRIPTION

Figure 1:
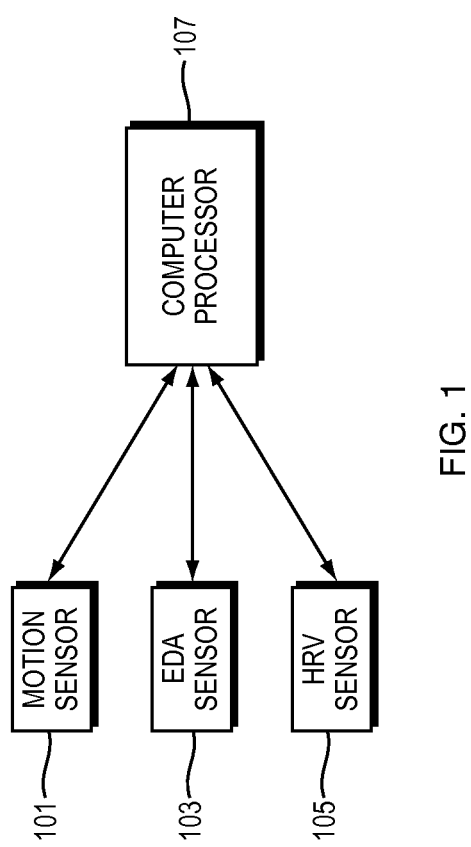
FIG. 1 is a block diagram of hardware that may be used to detect the onset of a tonic-clonic seizure.

FIG. 1 is a block diagram of hardware that may be used to detect the onset of a tonic-clonic seizure, in illustrative implementations of this invention. A motion sensor 101 and a sensor for taking electrodermal activity (EDA) measurements 103 gather sensor data. One or more computer processors 107 analyze this motion and EDA data, in order to detect the onset of the seizure. The motion sensor 101 may comprise a triple-axis accelerometer (ACM). The motion and EDA sensors may be housed in a comfortable, wrist-worn sensor package.

A sensor 105 may also gather HRV data. For example, the HRV sensor 105 may comprise an electrocardiograph.

The one or more processors 107 may analyze EDA and heart rate variability (HRV) data in order to assess autonomic activity, and based on that assessment, to evaluate a seizure. For example, the processors may use the EDA and HRV data: (a) to calculate the magnitude of autonomic response to a seizure; (b) to determine the severity of the seizure, and (b) to identify the seizure as being of a particular type (e.g., a generalized tonic-clonic seizure or a complex partial seizure).

In exemplary embodiments of this invention, one or more sensors take measurements before, during and after an epileptiform seizure. The sensor measurements are used to assess autonomic activity, including the autonomic response to the seizure. The sensor data is used to quantify both sympathetic and parasympathetic components of the autonomic activity. For example, electrodermal activity (EDA) measurements may be used to assess sympathetic activity, and heart rate variability (HRV) measurements may be used to assess parasympathetic activity.

In humans, sympathetic postganglionic fibers innervate eccrine sweat glands and their activity is reflected in measurable changes in skin conductance at the surface. Therefore, modulation in skin conductance, or more generally speaking, in electrodermal activity (EDA), is a parameter that reflects sympathetic activity.

In a prototype of this invention, a wearable sensor measures exosomatic EDA (skin conductance) by applying direct current to the stratum corneum of the epidermis beneath measuring electrodes. To achieve a wide dynamic range of skin conductance measurements, the analog conditioning circuitry utilizes non-linear feedback automatic bias control with low-power operational amplifiers. In addition, the sensor module also contains a triaxis accelerometer (ACM) for measurements of physical activity (actigraphy). A microcontroller digitizes the analog signals via a 12-bit A-D at a sampling frequency of 20 Hz. The data is then written to an onboard microSD card. The sensor module is integrated into a regular wristband made out of terrycloth, resulting in a comfortable and lightweight wearable sensor. All electronics and wiring are concealed within the wristband. The resulting device is inconspicuous, non-stigmatizing and allows for discrete monitoring of EDA. Furthermore, the electronic module can be easily detached when the user desires to wash the wristband.

In this prototype, the EDA sensor uses dry Ag/AgCl disc electrodes with contact areas of 1.0 cm$^2$ for recordings. These electrodes are disposable and can be snapped onto or removed from the wristband with ease. Preferably, the ventral side of the distal forearms is used as a recording site. Alternately, the electrodes may be placed on the palmar surface of the hand (e.g. medial and distal phalanges of the fingers and the thenar and hypothenar eminences). However, electrodes positioned on the forearm are less susceptible to motion artifacts than electrodes positioned on the palmar surface. A 3.7 V lithium polymer battery with a capacity of 1100 mAh provides around 40 hours of operation; the battery can be recharged via a micro-USB cable. In the prototype, both EDA and ACM recordings are sampled at 20 Hz. EDA recordings are analyzed using software written in MATLAB®.

The prototype can be employed to assess sympathetic response to a seizure, as follows: Raw EDA recordings are low-pass filtered (Hamming window, length=1025, 3 Hz) to reduce motion artifacts and the filtered signals are used in subsequent processing. For each seizure, the corresponding peri-ictal EDA recording from 60 min prior to EEG seizure onset up to 120 min afterwards is segmented. To obtain the time profile of EDA alterations, a one-minute moving average window with zero overlap is applied to the pre- and post-ictal segments. To calculate the ictal EDA parameters, the segmented recordings are low-pass filtered (Hamming window, length=1025, 0.01 Hz) to obtain the tonic component of EDA. The baseline is computed as the mean level over the entire 60 min pre-ictal period. Response latency is measured as the time from EEG seizure onset to the moment the filtered EDA signal exceeded two standard deviations (SD) above the pre-ictal baseline (EDA response onset). EDA response amplitude is determined as the difference between the response peak and pre-ictal baseline. Response end time is established as the time when the EDA response falls below 90% of the peak ictal amplitude. The area under the EDA response curve is calculated by integrating the EDA signal from the EDA response onset to the end time after subtracting the baseline. Area under the rising portion is taken as the integral from the EDA response onset to the peak response. The natural log-transformation is applied to all area calculations as the formation of the sum of products generates a value that increases and decreases in an exponential manner.

Figure 2:
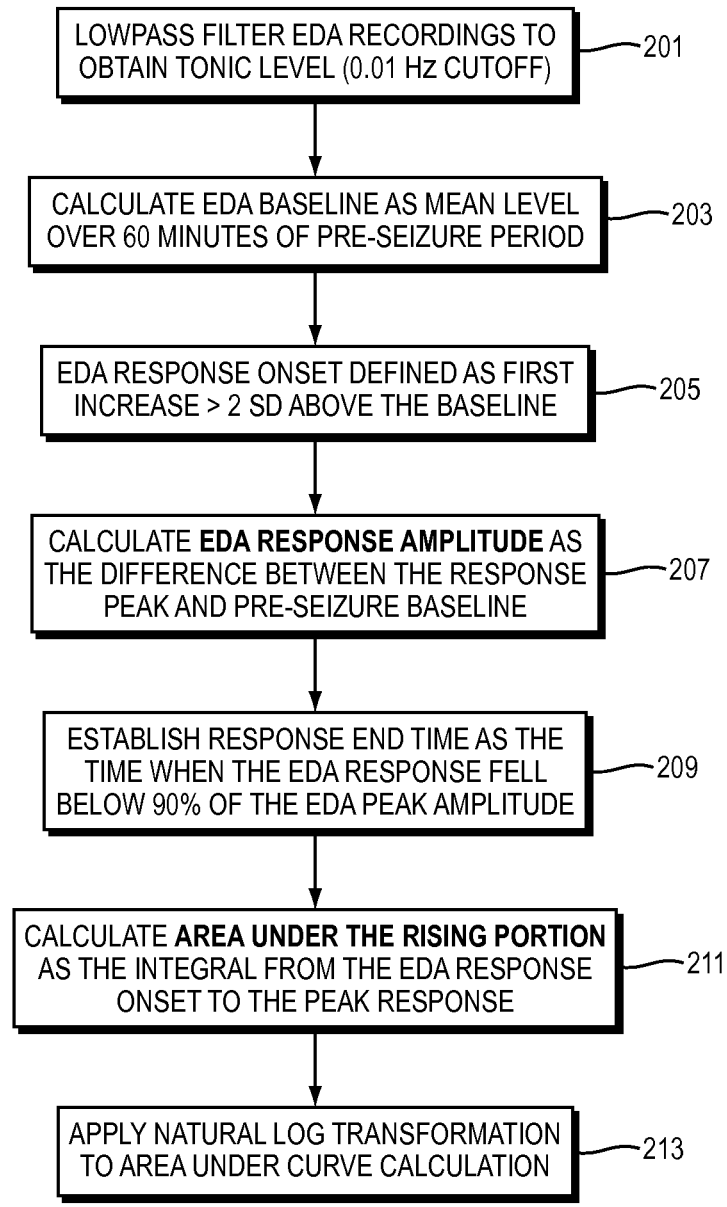
FIG. 2 is a flow chart that illustrates steps in assessing sympathetic response to a seizure.

FIG. 2 is a flow chart that illustrates steps in assessing sympathetic response to a seizure, in illustrative implementations of this invention. As shown in FIG. 2: EDA recordings are lowpass filtered to obtain a tonic level 201. An EDA baseline is calculated as a mean level over 60 minutes of pre-seizure period 203. The EDA response onset is defined as the time after the seizure at which EDA increases two standard deviations above the baseline 205. The EDA response amplitude is calculated as the difference between the response peak and the pre-seizure baseline 207. The response end time is identified as the time when the EDA response falls below 90% of the EDA peak amplitude 209. An area under the rising portion is calculated as the integral from the EDA response onset to the peak response 211. A natural log transformation is applied to the calculated area under the curve 213.

In exemplary implementations of this invention, heart rate variability (HRV) is used to assess parasympathetic activity, including parasympathetic response to a seizure. In particular, HRV is used to assess parasympathetic modulation of the heart. (In humans, the vagus nerve provides parasympathetic innervation to the sinoatrial node of the heart).

HRV is a measure of fluctuations in the inter-beat interval between normal heartbeats. One measure of the inter-beat interval is RRI. RRI measures the interval between two successive R spikes in a sequence of heart beats.

In exemplary implementations of this invention, the HF (high frequency) spectral component of an inter-beat interval signal is used to assess parasympathetic activity.

For example, in a prototype of this invention, parasympathetic activity is assessed as follows:

The inter-beat interval (RRI) time series is formed by first employing automated QRS detecting using filter banks and then examining the results to correct for false positives and missed beats. To remove artifacts such as ectopic beats, the RRI signal is filtered using the non-causal of variable threshold algorithm with a tolerance of 20%. Next, the RRI signal is interpolated using a cubic spline at 4 Hz to obtain a uniformly sampled time series. The time profile of heart rate alterations is computed as with a one-minute sliding window with no overlap that is applied to the pre- and post-ictal segments.

For time-frequency analysis, baseline non-stationarities of the RRI series are removed by a detrending method based on a smoothness priors approach with the smoothing parameter. The detrended RRI series is converted into an analytical signal using the Hilbert transform to remove negative frequencies. The smoothed pseudo Wigner-Ville (SPWV) time-frequency distribution with 1024 frequency bins is then computed using the analytical signal. A rectangular window (length=121) is used for time-domain smoothing. A Gaussian window is used for frequency smoothing (length=127).

The parasympathetic mediated high frequency spectral component (HF) is extracted from the SPWV distribution by integrating the spectral powers between 0.15 and 0.4 Hz. The time profile of HF power alterations is obtained using a one-minute moving average window with no overlap that is applied to the pre- and post-ictal segments. Pre-ictal baseline is determined by taking the mean value over the 30 min period right before EEG seizure onset. The minimum HF power level is also determined from the 30 min post-ictal period. The maximum percentage change in HF power is defined as:

$$\Delta HF_{max} = \frac{HF_{min} - HF_{baseline}}{HF_{baseline}} \times 100\% \quad \text{(Equation 1)}$$

where $HF_{min}$ is the minimum HF power level and $HF_{baseline}$ is the pre-ictal baseline min baseline value.

Figure 3:
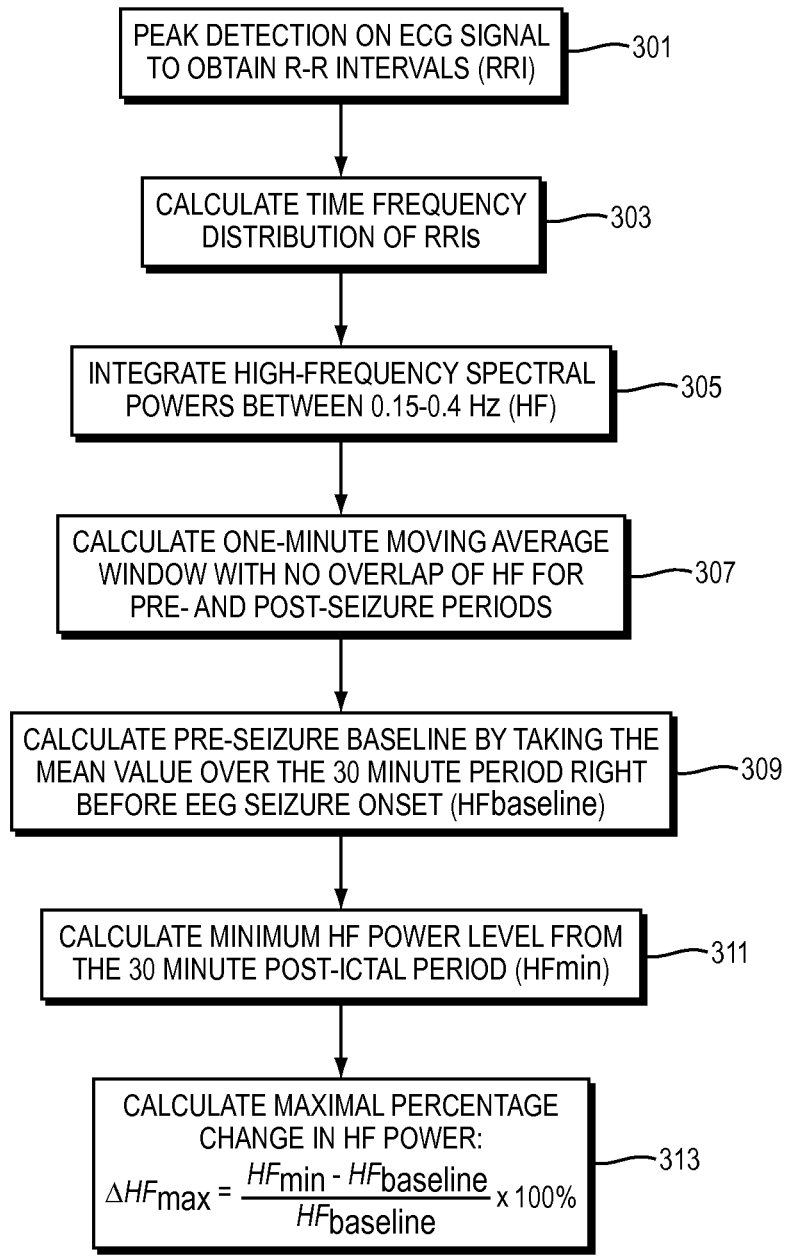
FIG. 3 is a flow chart that illustrates steps in assessing parasympathetic response to a seizure.

FIG. 3 is a flow chart that illustrates steps in assessing HRV response to a seizure, in illustrative implementations of this invention. As shown in FIG. 3: Peaks are detected 301 in an inter-beat interval signal. For example, the signal may be derived from ECG data or other sensor data indicative of heart beat. The time frequency distribution of the RRIs is calculated 303. High frequency spectral powers are integrated between 0.15 Hz and 0.4 Hz 305. The time profile of HF power alterations is obtained using a one-minute moving average window with no overlap for pre- and post-seizure periods 307. A pre-seizure baseline ($HF_{baseline}$) is calculated by taking the mean value over a 30 minute period before seizure onset 309. For example, seizure onset may be detected by EEG measurements. Of, for example, seizure onset may be detected by ACM and EDA measurements. A minimum HF power level ($HF_{min}$) is calculated from a 30 minute post-ictal period 311. A maximum percentage change in HF is calculated according to Equation 1 above 313.

In exemplary implementations of this invention, calculated measures of EDA and HRV activity are used to quantify autonomic activity. For example, the autonomic activity may comprise a response to an epileptiform seizure, and the EDA and HRV activity may be used to assess the seizure.

For example, in exemplary implementations of this invention, one or more processors analyze sensor data in order to calculate the magnitude of a post-ictal autonomic disturbance. Based on that calculated magnitude, the processors assess the severity of the seizure.

For example, the post-ictal autonomic disturbance may comprise a prolonged (e.g., at least 30 minutes) post-ictal surge in EDA and a prolonged, post-ictal decline in HF power. The processors may recognize such a EDA surge/HF power decline, and, based on that surge/decline, determine that: (a) the seizure is severe (e.g., has a higher rating on a severity scale than it would have been in the absence of such surge/decline); (b) the seizure is more likely to be a tonic-clonic seizure, and less likely to be a complex partial seizure; than it would have been in the absence of the surge/decline, or (c) the seizure has a higher risk of SUDEP (sudden unexpected death in epilepsy) than it would have in the absence of such a surge/decline.

For example, the processors may recognize a post-ictal autonomic disturbance lasting up to 100 minutes after tonic-clonic seizures, which disturbance may comprise two phases. The first phase may involve a prolonged sympathetic surge in EDA lasting approximately 65 minutes (indicating generalized sympathetic neural activation). The first phase may also involve a marked decrease in HF power (indicating a reduction of vagal parasympathetic control over the heart). The second phase may involve persistent low HF power and delayed decrease in heart rate even after sympathetic levels are restored to baseline (indicating impaired vagal reactivation).

For example, the processors may assess the seizure based on one or more of the following correlations: (a) the degree of both sympathetic activation and parasympathetic suppression increases approximately linearly with duration of post-ictal EEG suppression, (b) compared to complex partial seizures, generalized tonic-clonic seizures may induce much higher and prolonged sympathetic activation and greater reduction of cardiac vagal (parasympathetic) influence compared to complex partial seizures; (c) a period of disordered autonomic regulation after seizures, especially tonic-clonic seizures, may lead to increased vulnerability of a patient for sudden death (including SUDEP), and (d) tonic-clonic seizures at higher risk for SUDEP have significantly higher sympathetic activation and greater vagal reduction compared to tonic-clonic seizures in the lower risk group, and (e) seizure intensity as measured by autonomic dysregulation may be a factor in the pathogenesis of SUDEP. For example, the processors may treat autonomic footprints of seizures as biomarkers for the risk of SUDEP.

In exemplary implementations, this invention characterizes changes in EDA before, during and after epileptic seizures. Sympathetic EDA can be measured comfortably for long periods of time off the wrist. In some implementations, this invention can generate continuous, minute-by-minute profiles of both sympathetic and parasympathetic modulation for up to 2 hours after complex partial and secondarily generalized tonic-clonic seizures.

Figure 4:
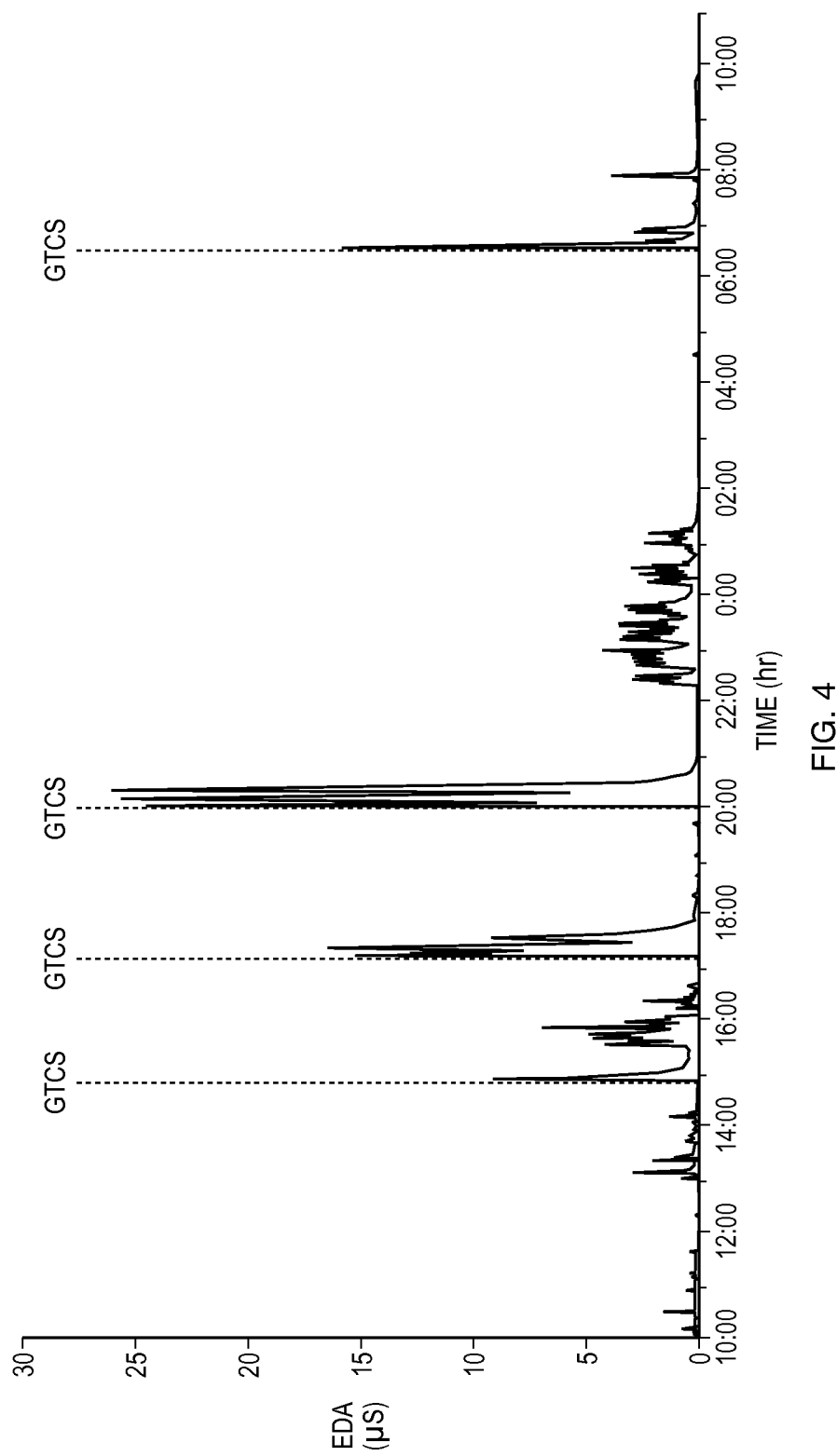
FIG. 4 shows an example of a 24 hour continuous EDA recording from a single patient, in which four secondarily generalized tonic-clonic seizures (GTCS) are captured.

FIG. 4 is a graph showing an example of long-term electrodermal activity (EDA) recordings that can be obtained from a wearable biosensor. In this example, a 24 h continuous EDA recording from a single patient is shown. Four secondarily generalized tonic-clonic seizures (GTCS) are shown. Dotted vertical lines denote EEG seizure onset.

Figure 5A:
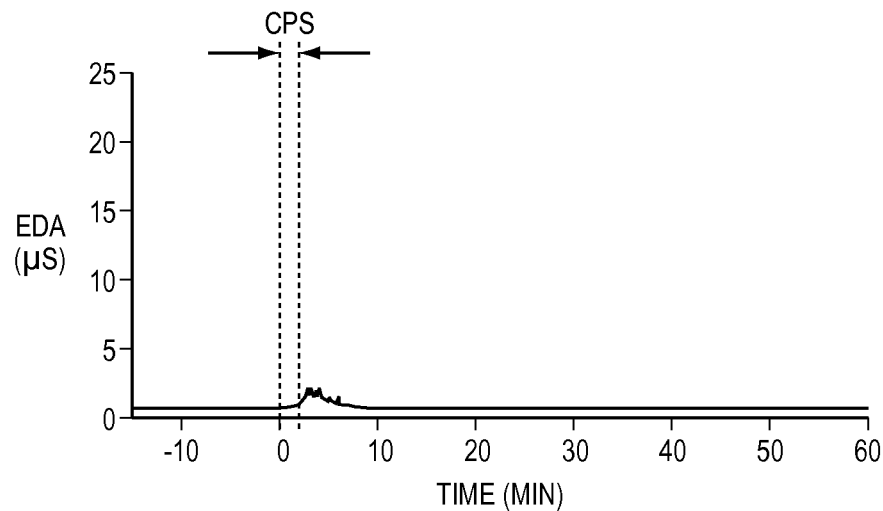
FIGS. 5A and 5B show examples of changes in EDA that can occur before, during and after individual epileptic seizures.
Figure 5B:
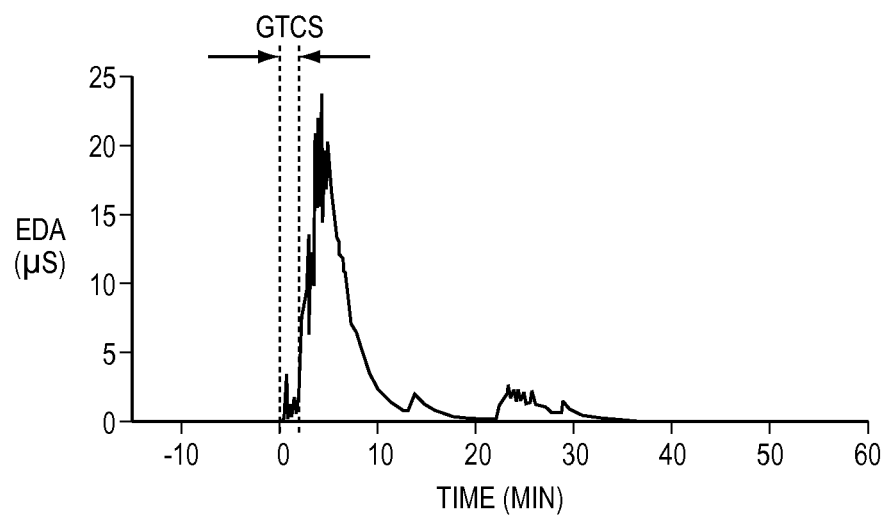

FIGS. 5A and 5B are graphs showing examples of changes in EDA that can occur before, during and after individual epileptic seizures. Dotted vertical lines denote EEG seizure onset and offset.

FIG. 5A shows a small increase of EDA during a complex partial seizure (CPS). There is also a decrease in RRI (i.e. increase in heart rate) and a brief reduction of the high frequency spectral component (HF, 0.15-0.4 Hz) of RRI during the post-ictal period that reappears after approximately 5 min. The decrease in RRI and reduction of HF component are not shown in FIG. 5A.

FIG. 5B shows a large surge in EDA after a secondarily generalized tonic-clonic seizure (GTCS). This surge is accompanied by a drop in RRI. RRI variability reduces during the post-ictal period and the high frequency power dramatically reduces. These reductions are not shown in FIG. 5B.

Figure 6A:
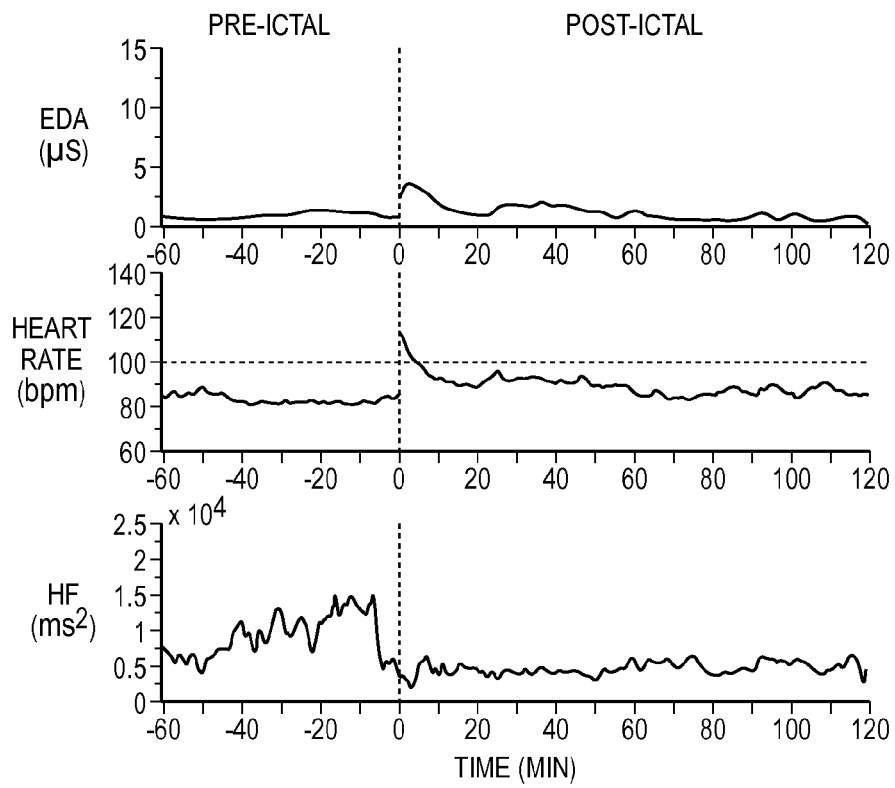
FIG. 6A shows an example of pre-ictal and post-ictal EDA, heart rate and HF power that can occur for complex partial seizures (CPS).
Figure 6B:
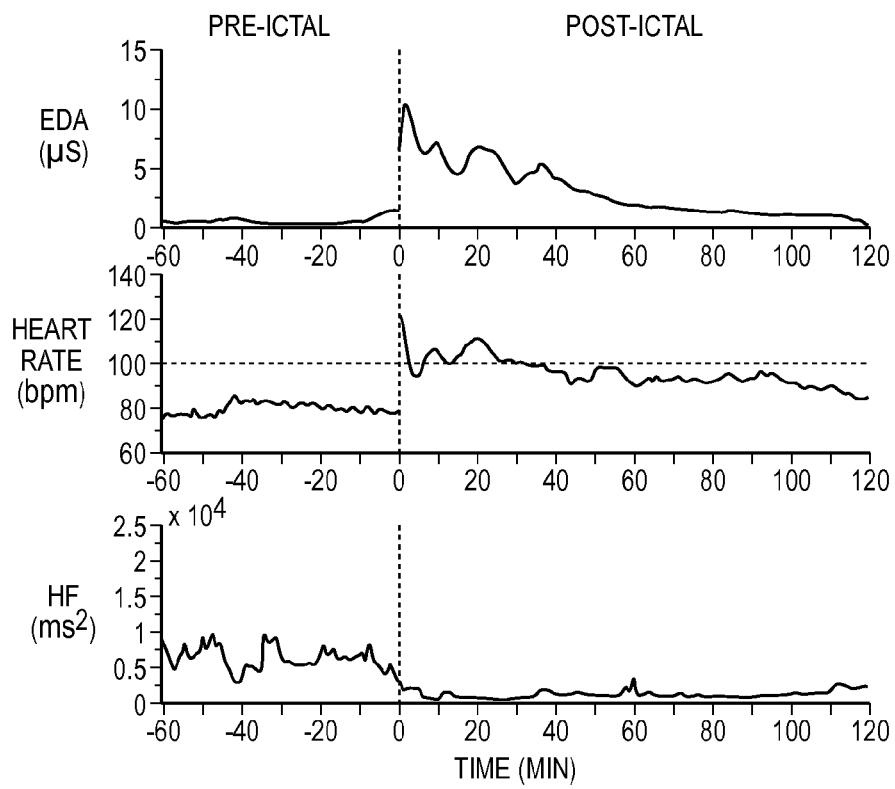
FIG. 6B shows an example of pre-ictal and post-ictal EDA, heart rate and HF power that can occur for generalized tonic-clonic seizures (GTCS).

FIGS. 6A, 6B, 6C, 6D are graphs showing an example of autonomic footprints of epileptic seizures. Profiles of autonomic alterations are computed every minute during a peri-ictal period of 3 h for complex partial seizures (FIG. 6A) and secondarily generalized tonic-clonic seizures (FIG. 6B). Each post-ictal measurement epoch is sequentially compared to the baseline level taken as the average of the entire 60 min pre-ictal period.

In the example shown in FIG. 6A, post-ictal levels of EDA are higher for 9 min after complex partial seizures ($p<0.05$, $n=22$). Heart rate is also higher lasting 3 min ($p<0.05$, $n=16$). HF power is continuously reduced for approximately 55 min ($p<0.05$, $n=16$). The first 56 min after tonic-clonic seizures is associated with marked increases in EDA ($p<0.05$, $n=12$) and heart rate ($p<0.05$, $n=10$), as well as profound reduction in HF power ($p<0.05$, $n=10$). Persistent tachycardia is observed for 40 min; heart rate and HF power levels recovered after 100 min.

Figure 6C:
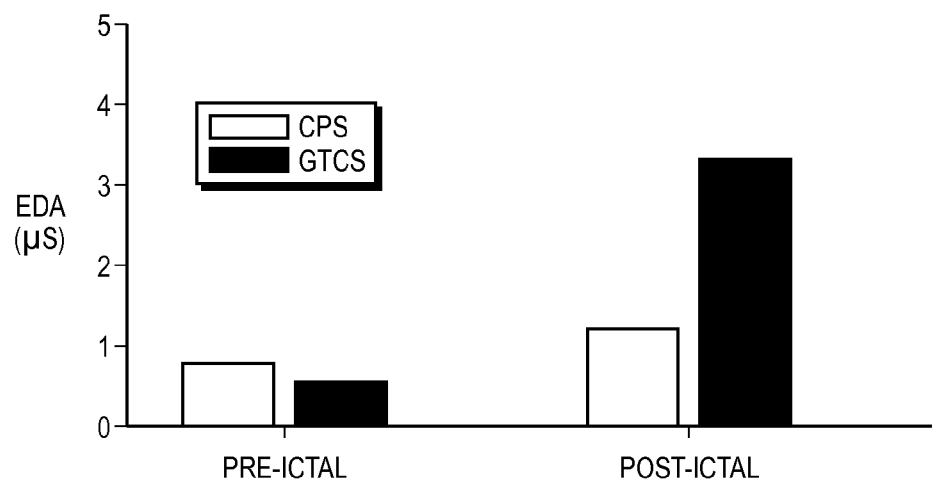
FIG. 6C shows an example of pre-ictal and post-ictal EDA levels that can occur in CPA and GTCS.

In the example shown in FIG. 6C, EDA during the pre-ictal period is marginally similar between CPS and GTCS ($p=0.05$; Mann-Whitney-Wilcoxon test [MWW]). However, EDA is higher in tonic-clonic seizures than in CPS during the first 60 min of the post-ictal period ($p=0.004$; MWW).

Figure 6D:
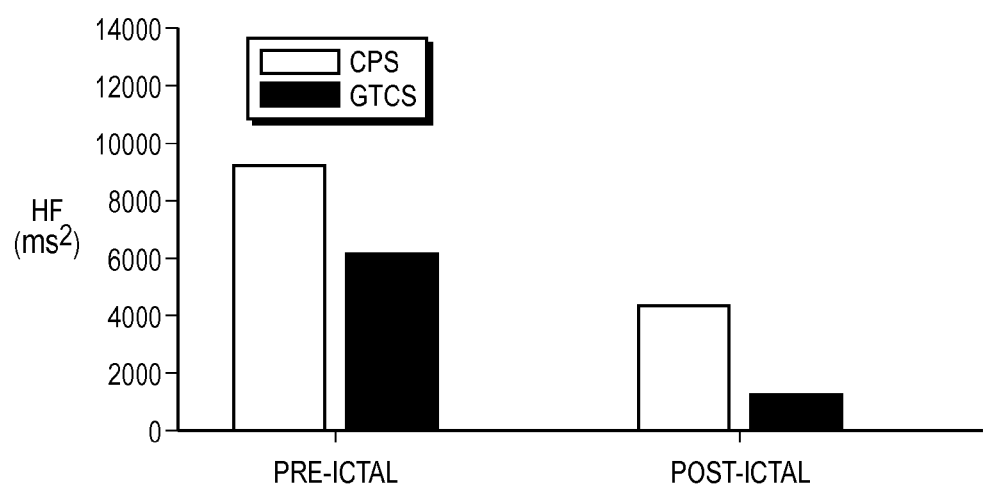
FIG. 6D shows an example of pre-ictal and post-ictal HF power levels that can occur in CPA and GTCS.

In the example shown in FIG. 6D, there is no difference in pre-ictal HF power between CPS and GTCS ($p>0.5$; MWW). Post-ictal HF power is lower in tonic-clonic seizures than in CPS ($p=0.033$; MWW).

FIGS. 7A, 7B, 7C, 7D, 7E are graphs that show an example of a relationship between degree of post-ictal autonomic disturbance and post-ictal generalized EEG suppression (PGES) in secondarily generalized tonic-clonic seizures (GTCS).

Figure 7A:
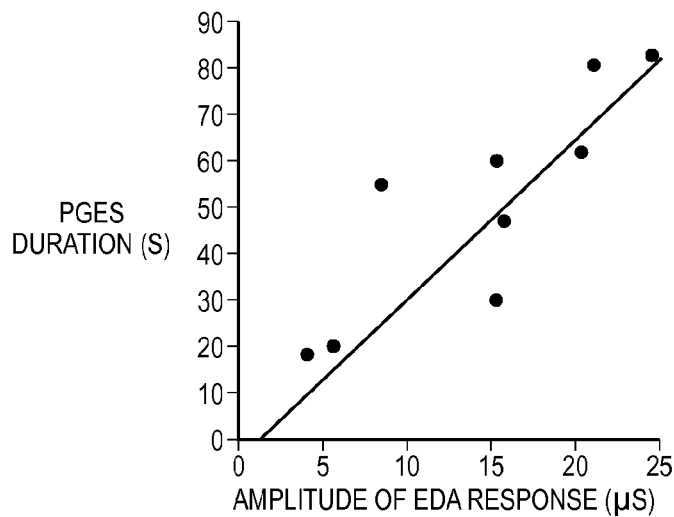
FIGS. 7A, 7B, 7C, 7D, 7E are graphs that show an example of a relationship that can occur between degree of post-ictal autonomic disturbance and post-ictal generalized EEG suppression (PGES) in generalized tonic-clonic seizures (GTCS).
Figure 7B:
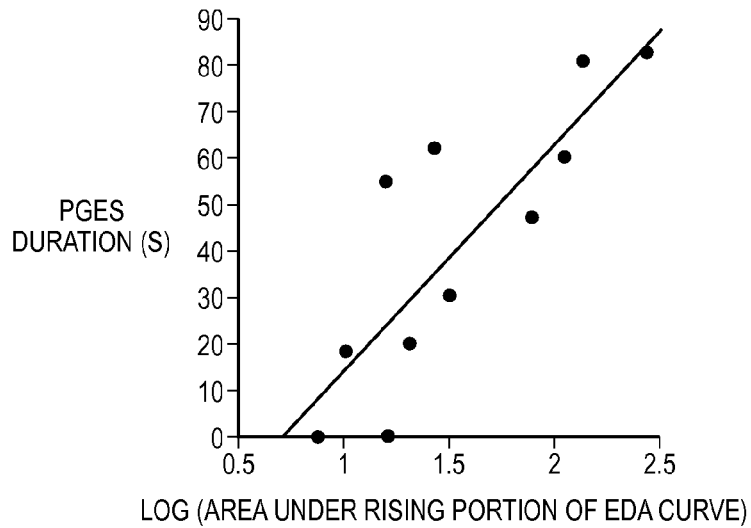
Figure 7C:
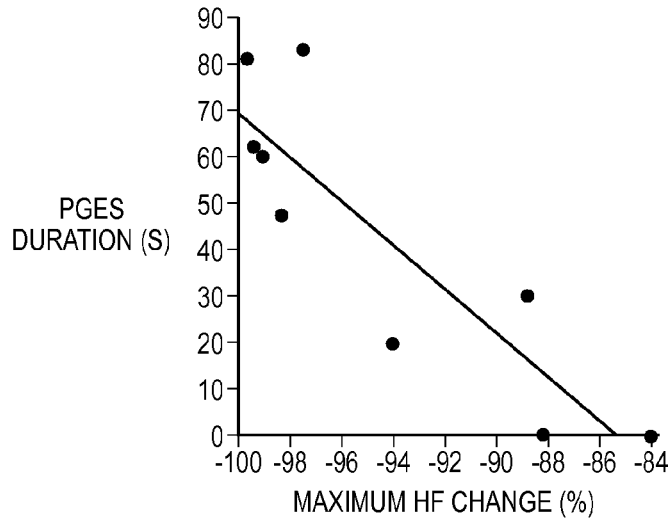

In this example, scatter plots show PGES duration versus: (a) EDA response amplitude (FIG. 7A); (b) log-transformed area under rising portion of EDA curve (FIG. 7B); and (c) maximum percentage HF power change (FIG. 7C). In this example, EDA response amplitude is strongly positively correlated with PGES (Pearson $r=0.81$, $p=0.003$; $n=11$), as is the area under rising portion of EDA curve ($r=0.83$, $p=0.002$; $n=11$). The reverse direction of relationship is observed for maximum percentage HF power change, which is strongly negatively correlated with PGES ($r=-0.87$, $p=0.002$; $n=9$).

Figure 7D:
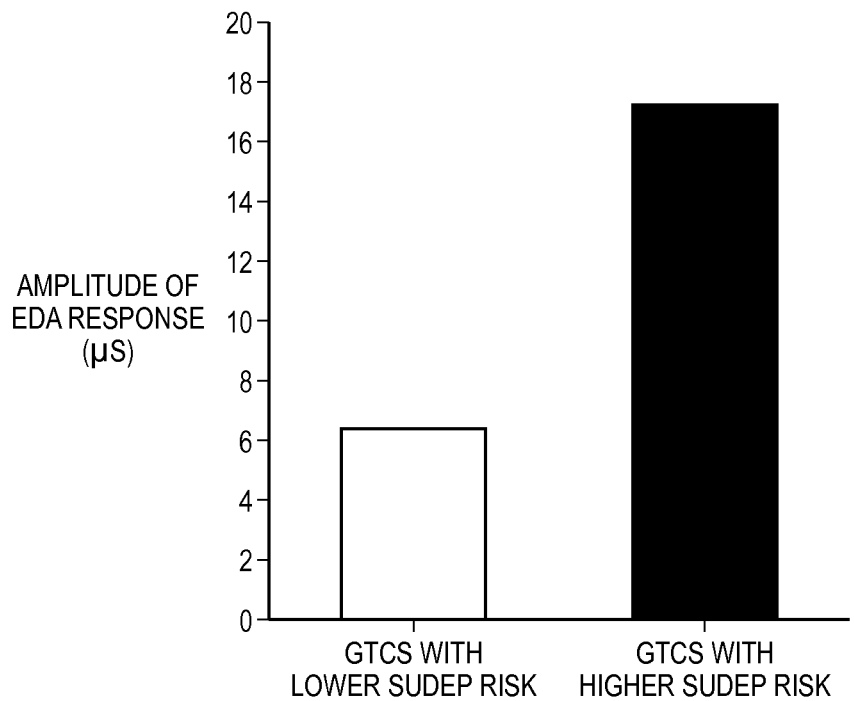

FIG. 7D shows an example in which EDA response amplitude is higher in GTCS with higher SUDEP risk (PGES>20 s) than in GTCS with lower SUDEP risk ($p=0.01$; Mann-Whitney-Wilcoxon test [MWW]).

Figure 7E:
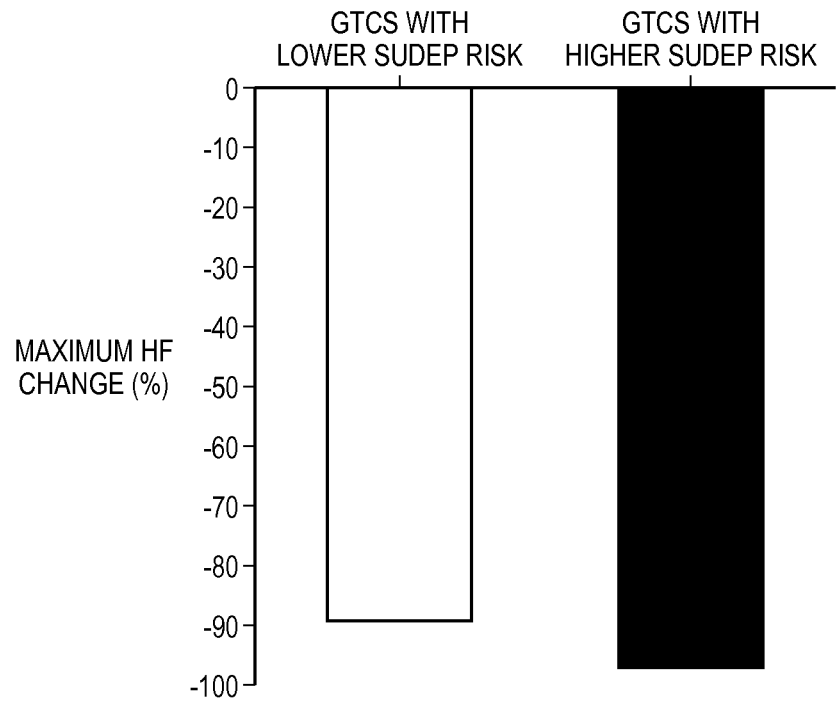

FIG. 7E shows an example in which the maximum percentage decrease in HF power is greater in GTCS with higher SUDEP risk than in GTCS with lower SUDEP risk ($p<0.05$; MWW).

Figure 8:
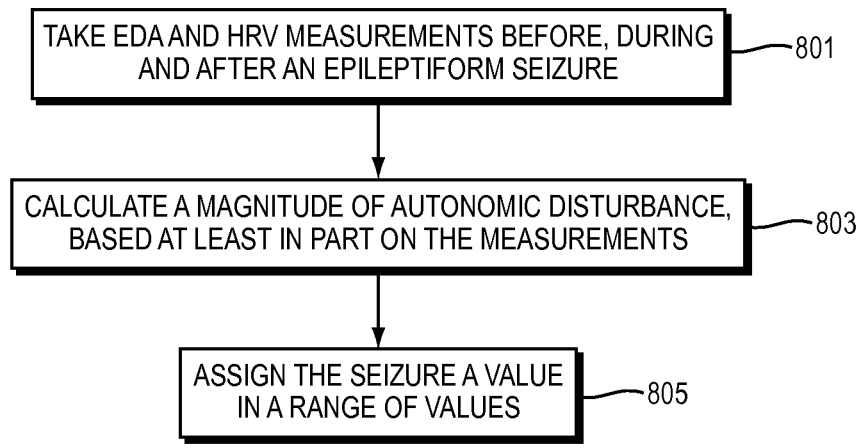
FIG. 8 is a high level flow chart that shows steps in assessing the severity of a seizure.

FIG. 8 is a high level flow chart of steps in assessing the severity of a seizure. As shown in FIG. 8, these steps may comprise: Take EDA and HRV measurements before and after an epileptiform seizure 801. Based at least in part on these measurements, calculate a magnitude of autonomic disturbance 803. Based at least in part on this calculated magnitude, assign the seizure a value in a range of values 805.

In exemplary implementations of this invention, a wearable device can provide round-the-clock monitoring to identify potentially dangerous seizures. This has many practical advantages: Among other things, in exemplary implementations, ambulatory monitoring of autonomic biomarkers of seizure intensity or SUDEP risk can be performed, without the need for continuous EEG measurements. Conventional EEG recorders tend to be unwieldy or stigmatizing. In contrast, the wrist-worn EDA biosensor used in a prototype of this invention allows comfortable round-the-clock monitoring without social awkwardness.

In exemplary implementations of this invention, a wearable sensor includes an EDA sensor, an onboard tri-axis accelerometer and wireless transceiver. The wearable sensor can be used for convulsive seizure detectors that can automatically alert caregivers in the event of a seizure. Furthermore, EDA parameters such as the amplitude of EDA response can provide caregivers with important information regarding the severity of the seizure and aid in the identification of seizures that require immediate medical attention.

In exemplary implementations, Support Vector Machines (SVM) are used to construct semi-patient-specific classifiers for sensitive and specific detection of GTC seizures. The problem of seizure detection is posed as a supervised learning task in which the goal is to classify a time series segment as seizure or non-seizure based on extracted features from EDA and ACM recordings. Analysis of ictal autonomic changes in EDA is used to supplement accelerometer-based motion analysis in order to enhance overall seizure detection performance.

Here is more detail regarding an EDA sensor used in a prototype of this invention. In this EDA sensor, automatic bias control uses two operation amplifiers. The first stage comprises an active low-pass filter (cutoff frequency $f_c=1.6$ Hz) with variable gain. To increase the dynamic range of measurements, the bias Vb of the first operational amplifier is determined by the feedback from the output of the second stage integrator $v_0$ (time constant $\tau=10$ ms). The applied voltage across the skin decreases in a non-linear fashion with increasing skin conductance. Although the current flow through the skin increases non-linearly with skin conductance, the current density is well below the recommended limit of 10 $\mu A/cm^2$; thus, there is minimal risk of damaging sweat glands. Within a range of skin conductance between 0.1 and 15 $\mu S$, the average voltage applied is 0.47 V and the average current flow is 2.37 $\mu A$. Overall, the skin resistance $R_{skin}$ can be calculated as follows:

$$R_{skin} = \frac{V_{cc} - V_b}{V_b - V_o} \qquad \text{(Equation 2)}$$

EDA measured as skin conductance can be obtained simply by taking the inverse of Equation 2.

In this prototype EDA sensor, DC is applied to the stratum corneum via surface contact dry electrodes for exosomatic measurements of EDA. To achieve a wide dynamic range of skin conductance measurements, the analog conditioning circuitry utilizes non-linear feedback automatic bias control with low-power operational amplifiers (LTC6081 by Linear Technology®). A triple-axis accelerometer (ADXL330 by Analog Devices®) is also included for physical activity measurements.

In this prototype, the EDA sensor is capable of recording measurements onto an on-board flash memory card (data logging), wirelessly transmitting data to a remote site (data forwarding) and performing real-time data processing.

A digital signal controller (dsPIC30F2012 by Microchip Technology®) acts as the control center that can be programmed on-board through an In-Circuit Serial Programming (ICSP) interface. Digital signal controllers (DSC) combine the control attributes of a microcontroller (MCU) and computation capabilities of a digital signal processor (DSP), thus allowing application specific real-time complex analysis on-board. The analog signals are sampled at 32 Hz via an A-D with 12-bit resolution on the DSC. Power is drawn from a single lithium polymer battery with a nominal voltage of 3.7 V and a capacity of 1100 mAh. The battery can be recharged directly from a USB port by an on-board single cell Li-Ion battery charger (LTC4062 by Linear Technology®). A step-up/step-down charge pump (LTC3240 by Linear Technology®) produces a fixed, regulated output of 3.3 V for the DSC and peripheral components.

In order to enable continuous measurements of EDA and physical activity without the constraint of staying within range of a base station, a data logging system may be available on board. Using a separate microcontroller with dedicated firmware to implement a FAT32 file system (uALFAT by GHI Electronics®) that communicates with the DSC through a UART (universal asynchronous receiver/transmitter) interface, data can be written to removable flash memory card. A 2G microSD card provides enough storage capacity for up to 28 days of continuous measurements with a sampling rate of 32 Hz. If it is desirable for the data to be accessible to the wearer's caregiver for analysis and interpretation, or if the wearer chooses to share his/her recordings, the EDA sensor can also operate as a data forwarding device with the use of a 2.4 GHz transceiver module (nRF2401A by Sparkfun Electronics®). In this mode, real-time measurements can be displayed on a PC equipped with a separate transceiver module for immediate analysis.

In this prototype EDA sensor, the electronic module is integrated into a regular wristband made out of terrycloth or other material, resulting in a comfortable, attractive and lightweight wearable sensor. Since all electronics and wiring are concealed within the wristband, the resulting device is also inconspicuous, non-stigmatizing and allows for discrete monitoring of EDA. Furthermore, the electronic module can be easily detached when the user desires to wash the wristband. The electrodes are disposable and can be snapped onto or removed from the wristband with ease.

Figure 9:
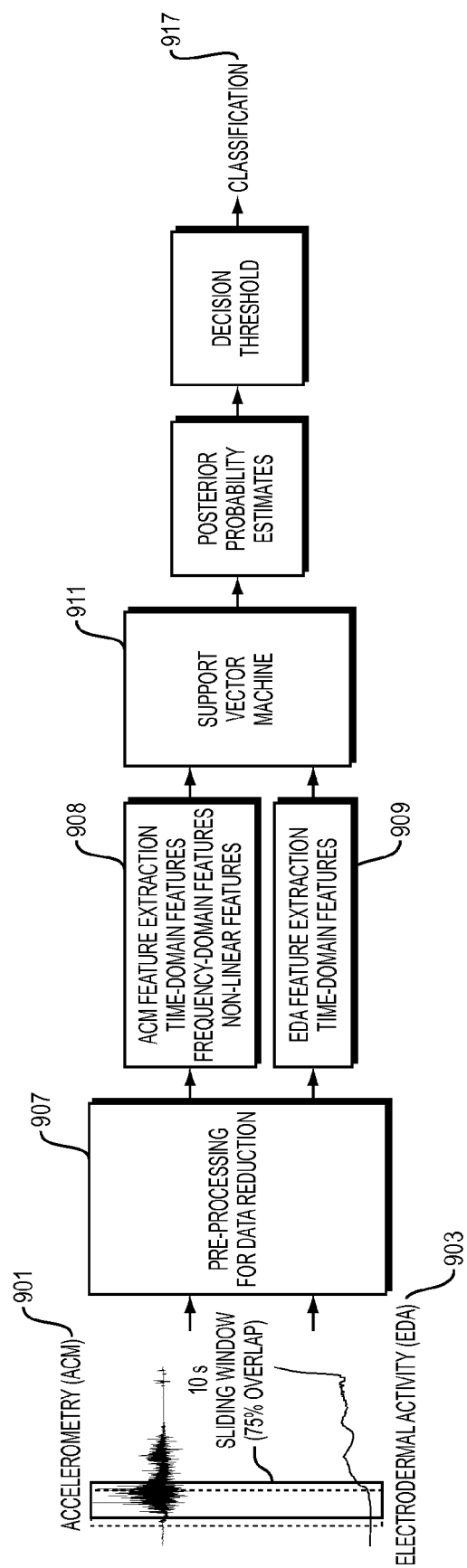
FIG. 9 is a high-level flow chart that shows steps in GTC (generalized tonic-clonic) seizure detection.

In exemplary implementations of this invention, GTC (generalized tonic-clonic) seizure detection comprises the steps shown in FIG. 9. A sliding window is used to extract 10 s epochs from both ACM and EDA recordings 901, 903 for each 2.5 s increment (75% overlap). The data is then pre-processed to removed non-motor and non-rhythmic epochs 907. Various features including time, frequency and non-linear features are extracted from remaining epochs of the ACM and EDA signals 908, 909. Finally, each feature vector comprising features from both ACM and EDA signals is assigned to a seizure or non-seizure class using a Support Vector Machine 911. A seizure is declared after one feature vector is assigned to the seizure class 917.

A GTC seizure typically lasts for 1-2 minutes whereas the patients can, in exemplary implementations, be monitored continuously for a long period of time. As such, there is a vast amount of non-seizure data (forming the majority class), which causes the data set to be highly imbalanced. Preferably, pre-processing of the data is performed to decrease the computational workload as well as reduce the degree of data imbalance during supervised learning.

Here is an example of GTC seizure detection in a prototype of this invention.

In this prototype implementation of GTC seizure detection, the first step is to divide the data into non-movement and movement events. Information from all three axes of the accelerometer is used to calculate the magnitude of the net acceleration, a as:

$$a = \sqrt{a_x^2 + a_y^2 + a_z^2}$$

A sliding window of 10 seconds with 75% overlap is used to calculate the standard deviation, $\sigma$ of the acceleration epoch ($a_1, a_2, \ldots, a_N$):

$$\sigma = \sqrt{\frac{1}{N}\sum_{i=1}^{N}(a_i - \mu)^2}$$

where $$\mu = \frac{1}{N}\sum_{i=1}^{N} a_i$$

Epochs with $\sigma$ below 0.1 g are automatically discarded from further analysis and treated as non-motor, and hence non-seizure events. The remaining epochs are detrended using a smoothness priors approach (smoothing parameter $\lambda = 300$) and the discrete Fourier transform (DFT) is computed.

GTC seizures are composed of two primary phases—the tonic phase and the clonic phase. The tonic phase involves stiffening of the limbs and flexion or extension of the neck, back and extremities. During the clonic phase, muscles of the entire body start to contract and relax rapidly. These convulsions are manifest in the ACM signal as rhythmic activity typically above 2 Hz. Thus, each epoch is evaluated for important periods. The underlying assumption is that the magnitudes of the coefficients of the DFT of a non-periodic time series are distributed according to an exponential distribution.

$$f(x) = \lambda e^{\lambda x}$$

Important periods will have powers that deviate from the power content of the majority of the periods and can be identified by locating outliers according to an exponential distribution. As a result, infrequent powers are sought by setting the probability p to a very low value to derive a power threshold $T_p$.

$$p = P(x \geq T_p) = e^{-\lambda T_p}$$

Solving for the power threshold, $$T_p = -\frac{\ln(p)}{\lambda}$$

For 99% confidence, set p=0.01. $\lambda$ is the reciprocal of the mean of the detrended acceleration signal power.

$$\frac{1}{\lambda} = \frac{1}{N}\sum_{i=1}^{N} a_i^2$$

Epochs with no frequency components that exceeded $T_p$ are discarded and labeled as non-seizure events. Otherwise, $f_{dominant}$, the frequency component with the highest power beyond $T_p$ is identified. If $f_{dominant} \geq 2$ Hz, the epoch is accepted for subsequent feature extraction.

In this prototype implementation, a total of 19 features are computed to characterize each measurement epoch. These features are chosen to describe the time, frequency and phase space characteristics of the ACM signal as well as the temporal traits of the EDA signal.

In this prototype implementation of GTC seizure detection, four different features are computed, in order to quantify the time-domain attributes of the ACM signal. These four features are the mean, standard deviation, and root mean-squared of the net acceleration. In addition, the amount of force is estimated by accumulating the magnitude of accelerometer data from each axis $a_{mag}$ throughout the 10 s epoch.

$$a_{mag} \int_n^{n+\Delta} |a_x(t)| + |a_y(t)| + |a_z(t)| dt$$

The major energy band for daily activities falls between 0.3 and 3.5 Hz whereas during GTC seizures the power is typically concentrated at frequencies above 2 Hz. In this prototype implementation, to capture the spectral information of the net acceleration, the net acceleration is detrended using a smoothness priors approach (smoothing parameter $\lambda=300$) and the power spectral density is computed using Welch's method (eight segments of equal length, 50% overlap, Hamming window). The entire frequency spectrum is divided into eight non-overlapping bands and the total integrated power within each spectral band is included as a feature (8 features). The dominant frequency within each epoch (across the entire 0 to 10 Hz band) and its maximum power are also computed as features (2 features). Thus, a total of 10 spectral features are included for classification.

Recurrence plots provide a graphical method designed to locate hidden recurring patterns and compute non-linear dynamical measures. This technique allows signals to be represented in state (phase) space by constructing embedded vectors $\vec{x}(k)$ using the method of time delays:

$$\vec{x}(k) = [x(k), x(k+d), \ldots, x(k+(m-1)d)]^T$$

where m is the embedding dimension and d is the time delay.

In this prototype implementation of GTC seizure detection, recurrence analysis is performed using the Recurrence Plot toolbox for Matlab®. The optimal parameter m=5 is chosen as the embedding dimension where the amount of false nearest neighbors approached zero. The delay d=1 is calculated from the first minimum of the mutual information function. The recurrence plot R(i, j) is then constructed by computing distances between all pairs of embedded vectors; a critical radius $\epsilon=1$ is established to create a binary plot showing, for a given moment in time, the times at which the state space trajectory visited roughly the same area in the state space.

$$R(i,j) = \Theta(\epsilon - \|\vec{x}(i) - \vec{x}(j)\|)$$

where $\Theta(x)$ is the Heaviside step function.

For example, in an illustrative recurrence plot constructed from a seizure epoch, short line segments parallel to the main diagonal suggest that the time series is deterministic. These small scale structures are quantified using recurrence quantification analysis. A feature included is the Shannon entropy ENTR of the lengths of the diagonal lines, which reflects the complexity of the deterministic structure in the system.

$$ENTR = -\sum_{l=l_{min}}^{N} p(l) \ln p(l)$$

where p(l) is the probability that a diagonal line has exactly length l estimated from the histogram P(l) of the lengths l of the diagonal lines.

$$p(l) = \frac{P(l)}{\sum_{l=l_{min}}^{N} P(l)}$$

Another feature computed is laminarity LAM, the percentage of recurrence points which formed vertical lines. LAM is related with the amount of laminar phases in the system (intermittency).

$$p(l) = \frac{P(l)}{\sum_{l=l_{min}}^{N} P(l)}$$

where P(v) is the histogram of the lengths v of the vertical lines.

To summarize, in this prototype implementation of GTC detection, 16 ACM features are computed including 4 time-domain (mean, standard deviation, root mean-squared and accumulated magnitude), 10 spectral (dominant frequency, maximum power, and integrated power values from 8 non-overlapping frequency bands) and 2 non-linear features (entropy and laminarity).

In this prototype implementation of GTC detection, EDA analysis is performed as follows:

First, the EDA recordings are lowpass filtered (Hamming window, length=1025, 3 Hz) to reduce artifacts. Since GTC seizures are associated with an increase in EDA, three features are extracted from each 10 s EDA epoch. A linear least squares fit to the EDA segment is performed. The slope is computed as the first feature. The number of measurement points within the epoch that are greater than the previous point (i.e. x(n)>x(n-1)) is determined as the second feature. The third feature corresponds to the difference between the EDA measured at the start and end of the 10 s epoch.

In this prototype implementation of GTC detection, Support Vector Machines (SVMs) are employed. SVMs are binary classification methods that exhibit a remarkable resistance to overfitting and have shown excellent performance in complicated pattern recognition problems. An SVM can learn a decision boundary in the form of a hyperplane that separates two classes. This hyperplane is selected such that the classification margin, which is the geometric distance between the hyperplane and the boundary cases of each class (i.e. the support vectors), is maximized for the best ability to accurately classify unseen data. Moreover, SVMs can map the original finite dimensional feature space into a much higher dimensional space through the use of a kernel function to improve the separability of the data.

An SVM is a good choice for the task of seizure detection because its unique learning mechanism allows it to perform well with moderately imbalanced data without any modifications. Since an SVM only takes into account those instances that are close to the boundary for building its model, it is unaffected by negative instances far away from the boundary even if they are large in number. This is important given that the number of non-seizure instances far outnumber the seizure instances.

In this prototype, designing the SVM algorithm for seizure detection consists of a training phase, in which the model is learned on a subset of data and a testing phase, in which the model performance is evaluated on a different subset of data. The Gaussian Radial Basis kernel function (RBF) is chosen as it provides non-linear mapping of the original feature vectors $\vec{y}_i$ into a higher dimensional space.

$$\text{RBF}: K(\vec{y}_i, \vec{y}_j) = \exp(-\gamma \|\vec{y}_i - \vec{y}_j\|^2), \gamma > 0$$

In this prototype, overall, the SVM model required two parameters to be chosen: the penalty ("soft margin") parameter of the error term C which specifies the trade-off between maximizing the classification margin and minimizing the training error, and the RBF kernel parameter γ which controls the curvature of the hyperplane. SVMs can be implemented using LibSVM, a publicly available software library for support vector classification. Each feature in the training data is linearly scaled to the range [0, 1] to assure commensurability of the various features before applying SVM. The same scaling template is applied to the testing data before performing classification.

In this prototype implementation of GTC detection, the problem of seizure detection is posed as a supervised learning task in which the goal is to classify each 10 s epoch as seizure or non-seizure based on extracted features from EDA and ACM recordings. If any epoch between the start and end of a labeled seizure is correctly classified as a seizure event, the seizure is considered to be detected (true positive). If multiple epochs within the seizure duration are detected, these are treated as a single correct detection event. False detections that occurred within 30 s apart from each other are treated as a single false alarm.

In exemplary implementations of this invention, EDA signals supplement ACM signals for seizure detection.

In some implementations, this invention further comprises an EEG recording system. The EEG recording system may be ambulatory (in the form of a backpack), so that patients are not constrained to staying in bed but could walk around the room, go over to a playroom nearby or leave the LTM for imaging studies and other tests In some implementations, a non-patient-specific seizure (generic) GTC detection mode is used to assess the baseline performance on unseen patients. In other implementations, an adaptive approach for GTC detection is used, which includes previous examples of seizures from the test patient in training. The adaptive, or semi-patient-specific mode may produce superior performance compared to the generic mode. Since the GTC seizure manifestation in ACM and EDA signals may vary from patient to patient, it is reasonable that an adaptive approach which takes advantage of the consistency of an individual patient's unique seizure signature as well as typical non-seizure activity patterns improves performance. For practical use, the generic mode is important for a seizure detector to be of immediate use to every patient right "out of the box". As more examples of seizures are obtained over time, the algorithm can then improve by machine learning and become more customized for each particular patient.

In exemplary implementations of this invention, incorporating EDA measurements in a seizure detector improves detection performance as well as provides a quantitative measure of the autonomic impact for each seizure.

In exemplary implementations of this invention, one or more computers or electronic processors are employed. For example, these computers or processors may be used for computing operations, including receiving input data, performing calculations, and generating control signals. The one or more computers or processors (e.g., 107 in FIG. 1) may be positioned in any configuration, including a configuration in which at least some of the processors are remote from the remainder of the processors (or from a human patient). The one or more processors may, for example, communicate wirelessly or by wired connection.

In some embodiments, various methods described herein may be included in a computer program product from a computer-readable storage medium and this medium may be internal or external, removable and replaceable, or fixed.

DEFINITIONS AND CLARIFICATIONS

Here are a few definitions and clarifications. As used herein:

The terms "a" and "an", when modifying a noun, do not imply that only one of the noun exists.

"EDA" means electrodermal activity.

An "EDA value" includes either (a) a measured EDA value, or (b) a measured EDA value minus a baseline or reference EDA value.

"ECG" means electrocardiogram.

The term "epileptiform" seizures includes epileptic seizures.

"HRV" means heart rate variability.

"Heart rate variability" includes heart rate variability or any other parameter (including heart rate) of a heart beat signal.

"High frequency" means within a frequency range, which range has a lower bound that is not less than 0.1 and an upper bound that is not more than to 0.5 Hz.

The term "include" shall be construed broadly, as if followed by "without limitation".

An "inter-beat interval" is an interval between successive heart beats. For example, an RRI is an inter-beat interval.

The term "or" is an inclusive disjunctive. For example "A or B" is true if A is true, or B is true, or both A or B are true.

A parenthesis is simply to make text easier to read, by indicating a grouping of words. A parenthesis does not mean that the parenthetical material is optional or can be ignored.

"Power" includes any measure of signal size, including signal power or signal energy.

"RRI" means an interval between two successive R spikes in a sequence of heart beats.

"SUDEP" means a death that satisfies the criteria for SUDEP (sudden unexpected death in epilepsy) developed by the US Food and Drug Administration and Burroughs-Wellcome in 1993.

Assigning something (e.g., seizure or atypical electrical brain activity) a "value out of a range of values" includes (a) assigning it as belonging to a class out of a set of classes, or (b) assigning it a value out of a set of values.

To the extent that terms used herein are explicitly defined herein or explicitly clarified herein, the explicit definitions and explicit clarifications control. To the extent that terms used herein are not expressly defined herein or expressly clarified herein, the terms have the meanings that they had as of May 17, 2012, and shall not be affected by any change in terminology occurring after May 17, 2012.

Variations

This invention may be implemented in many different ways. Here are some non-limiting examples:

This invention is not limited to the assessment of epileptic seizures. Instead, in some implementations, this invention can be used to assess any atypical electrical brain activity (AEBA). For example, the AEBA may comprise an epileptic seizure (including a partial seizure, generalized seizure, simple seizure, complex seizure, complex partial seizure or generalized tonic-clonic seizure). Or, for example, the AEBA may comprise any other type of epileptiform seizure, ictal or inter-ictal electrical brain activity, cortical or sub-cortical electrical brain activity, or suppression of electrical brain activity. The assessment of an ABEA may include assigning the ABEA a value in a range of values.

In some implementations, this invention may be used to quantify autonomic footprints occurring before, during or after ABEA (or between ABEAs). For example, in some implementations, this invention may be used to quantify the magnitude of autonomic disturbance following an ABEA.

This invention may be used, in some implementations, to assess a mortality risk. For example, it could be used to assess a risk of sudden death occurring after an epileptic seizure (for example, SUDEP or sudden death that occurs hours after a seizure).

This invention is not limited to analysis in a particular domain. Depending on the particular implementation, analysis may for example be performed in any one or more of the following: time domain, frequency domain, and LaPlace domain.

This invention may be implemented as a method, comprising, in combination: (a) using one or more sensors to take EDA measurements of a human before and after atypical electrical brain activity of the human, and (b) using one or more computer processor (i) to calculate, based at least in part on at least some of the EDA measurements, a magnitude of autonomic disturbance, which autonomic disturbance comprises a change in EDA occurring after the atypical electrical brain activity; and (ii) to assign, based at least in part on the magnitude of the autonomic disturbance, the atypical electrical brain activity a value in a range of values. Furthermore: (1) the atypical electrical brain activity may include an epileptiform seizure; (2) the epileptiform seizure may comprise an epileptic seizure; (3) the atypical electrical brain activity may include at least one of ictal electrical brain activity and inter-ictal electrical brain activity; (4) the atypical electrical brain activity may include at least one of cortical and sub-cortical electrical brain activity; (5) the atypical electrical brain activity may include a difference between left and right brain portions; (6) the one or more sensors may further measure EDA activity during the atypical electrical brain activity, and the autonomic disturbance may further comprise a change in EDA during the atypical electrical brain activity; (7) the value in a range of values may comprise a class out of a set of classes, and the set of classes may include a first class that comprises types of tonic-clonic seizures and a second class that comprises types of partial-complex seizures; (8) the method may further comprise taking HRV measurements of the human before and after the atypical electrical brain activity, and the autonomic disturbance may further comprise a change in HRV; (9) the atypical electrical brain activity may comprise electrical brain activity suppression; (10) different values in the range of values may be indicative of different levels of a mortality risk; (11) different values in the range of values may be indicative of different levels of risk of SUDEP; (12) autonomic disturbance may be calculated based, at least in part, on an integral of EDA values during a period that occurs after the atypical electrical brain activity; (13) autonomic disturbance may be calculated based at least in part on time-domain analysis of an inter-beat interval signal; (14) the autonomic disturbance may be calculated based at least in part on analysis of an inter-beat interval signal, the signal may include a high frequency spectral component, the power of the high frequency spectral component may have a minimum during a period after the atypical electrical brain activity, and the autonomic disturbance may be calculated based, at least in part, on the minimum; (15) the autonomic disturbance may be calculated based, at least in part, on either (a) a maximum percentage change in the power of the high frequency spectral component during the period, defined as:

$$\Delta HF_{max} = \frac{HF_{min} - HF_{baseline}}{HF_{baseline}} \times 100\%$$

where $HF_{min}$ is the minimum, and $HF_{baseline}$ is a baseline value of the power of the high frequency spectral component, or (b) any number (including $\Delta HF_{max}/100\%$) that is max proportional to $\Delta HF_{max}$; (16) the one or more processors may treat at least one EDA max pattern as a biomarker for a particular level of a mortality risk or as a biomarker for at least some tonic-clonic seizures; (17) the one or more processors may treat at least one HRV pattern as a biomarker for a particular level of a mortality risk or as a biomarker for at least some tonic-clonic seizures; and (18) at least some of the one or more sensors may be wearable, the one or more sensors may include a motion sensor, and the one or more processors may further detect, based at least in part on the input data, onset of a tonic-clonic seizure.

This invention may be implemented as apparatus comprising: (a) one or more sensors for taking EDA measurements of a human before and after an epileptiform seizure of the human; and (b) one or more computer processors for: (i) calculating, based at least in part on at least some of the EDA measurements, a magnitude of autonomic disturbance, which autonomic disturbance comprises a change in EDA occurring after the seizure; and (ii) assigning, based in least in part on the magnitude of autonomic disturbance, the seizure a value in a range of values. Furthermore: (1) the apparatus may further comprise one or more sensors for taking HRV measurements of the human before, during and after the seizure, the autonomic disturbance may further comprise a change in HRV, and the one or more processors may be further adapted to calculate the magnitude of autonomic disturbance based, in part, on the HRV measurements; (2) the one or more processors may be adapted to treat at least one EDA pattern as a biomarker for a particular level of a mortality risk or as a biomarker for at least some tonic-clonic seizures; (3) the one or more processors may be adapted to treat at least one HRV pattern as a biomarker for a particular level of a mortality risk or as a biomarker for at least some tonic-clonic seizures; and (5) at least one of the sensors may be further adapted to measure EDA during the seizure, and the autonomic disturbance may further comprise a change in EDA during the seizure.

This invention may be implemented as a computer program product for seizure detection, embodied in a non-transitory computer readable medium, comprising: (a) code for taking EDA measurements of a human before and after atypical electrical brain activity of the human, (b) code for calculating, based at least in part on at least some of the EDA measurements, a magnitude of autonomic disturbance occurring after the atypical electrical brain activity; and (c) code for assigning, based at least in part on the magnitude of the autonomic disturbance, the atypical electrical brain activity a value in a range of values.

CONCLUSION

It is to be understood that the methods and apparatus which have been described above are merely illustrative applications of the principles of the invention. Numerous modifications may be made by those skilled in the art without departing from the scope of the invention. The scope of the invention is not to be limited except by the claims that follow.

What is claimed is:

1. A method, comprising, in combination:
   (a) one or more sensors taking EDA (electrodermal activity) measurements of a human before and after an epileptiform seizure of the human, including during at least part of a 10 minute interval immediately after the seizure, and
   (b) one or more computer processors
   (i) calculating, based at least in part on at least some of the EDA measurements, a magnitude of autonomic disturbance, which autonomic disturbance comprises a change in EDA occurring after the seizure, and
   (ii) assigning, based at least in part on the magnitude of the autonomic disturbance, the seizure a value in a range of values, which value is indicative of risk of SUDEP.

2. The method of claim 1 wherein the epileptiform seizure comprises an epileptic seizure.

3. The method of claim 1 wherein the seizure includes at least one of ictal electrical brain activity and inter-ictal electrical brain activity.

4. The method of claim 1 wherein the seizure includes at least one of cortical and sub-cortical electrical brain activity.

5. The method of claim 1 wherein the seizure includes a difference between left and right brain portions.

6. The method of claim 1 wherein
   the one or more sensors further measure EDA activity during the seizure, and
   the autonomic disturbance further comprises a change in EDA during the seizure.

7. The method of claim 1, wherein:
   (a) the method further comprises using the one or more processors to assign the seizure into a class out of a set of classes, and
   (b) the set of classes includes a first class that comprises types of tonic-clonic seizures and a second class that comprises types of partial-complex seizures.

8. The method of claim 1, wherein:
   the method further comprises taking HRV measurements of the human before and after the seizure; and
   the autonomic disturbance further comprises a change in HRV.

9. The method of claim 1 wherein the autonomic disturbance comprises electrical brain activity suppression.

10. The method of claim 1, wherein the autonomic disturbance is calculated based, at least in part, on an integral of EDA values during a period that occurs after the seizure.

11. The method of claim 8, wherein the autonomic disturbance is calculated based, at least in part, on an integral of EDA values during a period that occurs after the seizure.

12. The method of claim 11, wherein the autonomic disturbance is calculated based at least in part on time-domain analysis of an inter-beat interval signal.

13. The method of claim 8, wherein
   the autonomic disturbance is calculated based at least in part on analysis of an inter-beat interval signal,
   the signal includes a high frequency spectral component,
   the power of the high frequency spectral component has a minimum during a period after the seizure, and
   the autonomic disturbance is calculated based, at least in part, on the minimum.

14. The method of claim 13, wherein the autonomic disturbance is calculated based, at least in part, on a maximum percentage change in the power of the high frequency spectral component during the period, defined as:

$$\Delta HF_{max} = \frac{HF_{min} - HF_{baseline}}{HF_{baseline}} \times 100\%$$

where $HF_{min}$ is the minimum, and $HF_{baseline}$ is a baseline value of the power of the high frequency spectral component.

15. The method of claim 1, wherein the one or more processors treat at least one EDA pattern as a biomarker for at least some tonic-clonic seizures.

16. The method of claim 15, wherein the one or more processors treat at least one HRV pattern as a biomarker for a particular level of a mortality risk or as a biomarker for at least some tonic-clonic seizures.

17. The method of claim 1, wherein:
   at least some of the one or more sensors are wearable,
   the one or more sensors include a motion sensor, and
   the one or more processors further detect, based at least in part on the input data, onset of a tonic-clonic seizure.

18. An apparatus comprising:
   (a) one or more sensors for taking EDA (electrodermal activity) measurements of a human before and after an epileptiform seizure of the human, including during at least part of a 10 minute interval immediately after the seizure; and
   (b) one or more computer processors programmed for
   (i) calculating, based at least in part on at least some of the EDA measurements, a magnitude of autonomic disturbance, which autonomic disturbance comprises a change in EDA occurring after the seizure, and
   (ii) assigning, based at least in part on the magnitude of the autonomic disturbance, the seizure a value in a range of values, which value is indicative of risk of SUDEP.

19. The apparatus of claim 18, wherein:
   the apparatus further comprises one or more sensors for taking HRV measurements of the human before, during and after the seizure,
   the autonomic disturbance further comprises a change in HRV, and
   the one or more processors are further adapted to calculate the magnitude of autonomic disturbance based, in part, on the HRV measurements.

20. The apparatus of claim 18, wherein the one or more processors are adapted to treat at least one EDA pattern as a biomarker for at least some tonic-clonic seizures.

21. The apparatus of claim 18, wherein the one or more processors are adapted to treat at least one HRV pattern as a biomarker for a particular level of a mortality risk or as a biomarker for at least some tonic-clonic seizures.

22. A computer program product for seizure detection, embodied in a non-transitory computer readable medium, comprising:
   code for taking EDA (electrodermal activity) measurements of a human before and after an epileptiform seizure of the human,
   code for calculating, based at least in part on at least some of the EDA measurements, a magnitude of autonomic disturbance, which autonomic disturbance comprises a change in EDA occurring during at least part of a 10 minute period immediately after the seizure; and code for assigning, based at least in part on the magnitude of the autonomic disturbance, the seizure a value in a range of values, which value is indicative of risk of SUDEP.

* * * * *

UNITED STATES PATENT AND TRADEMARK OFFICE
CERTIFICATE OF CORRECTION

| | | |
|---|---|---|
| PATENT NO. | : 8,795,173 B2 | Page 1 of 1 |
| APPLICATION NO. | : 13/474704 | |
| DATED | : August 5, 2014 | |
| INVENTOR(S) | : Ming-Zher Poh et al. | |

It is certified that error appears in the above-identified patent and that said Letters Patent is hereby corrected as shown below:

Title page

Item 75, Inventors should read

Ming-Zher Poh, Cambridge, MA (US);
Rosalind Picard, Newton, MA (US);
Tobias LoddenKemper, Natick, MA (US)

Signed and Sealed this
Twenty-fifth Day of August, 2015

Michelle K. Lee
*Director of the United States Patent and Trademark Office*

UNITED STATES PATENT AND TRADEMARK OFFICE
CERTIFICATE OF CORRECTION

PATENT NO. : 8,795,173 B2
APPLICATION NO. : 13/474704
DATED : August 5, 2014
INVENTOR(S) : Ming-Zher Poh et al.

Page 1 of 1

It is certified that error appears in the above-identified patent and that said Letters Patent is hereby corrected as shown below:

Title page

Item 75, Inventors should read

Ming-Zher Poh, Cambridge, MA (US);
Rosalind Picard, Newton, MA (US);
Tobias Loddenkemper, Natick, MA (US)

This certificate supersedes the Certificate of Correction issued August 25, 2015.

Signed and Sealed this
First Day of December, 2015

Michelle K. Lee
*Director of the United States Patent and Trademark Office*